United States Patent [19]

Sawa et al.

[11] Patent Number: 5,021,584

[45] Date of Patent: Jun. 4, 1991

[54] PROCESS FOR PREPARATION OF 1-BENZYLIMIDAZOLE COMPOUND

[75] Inventors: Natsuo Sawa, Tadotsu; Takeshi Masuda, Marugame; Shozo Miura, Mino; Naoki Kano, Marugame; Kazuo Kamagata, Hatoyama; Masayuki Ito, Sakado, all of Japan

[73] Assignee: Shikoku Chemicals Corporation, Kagawa, Japan

[21] Appl. No.: 403,460

[22] Filed: Sep. 6, 1989

[30] Foreign Application Priority Data

Sep. 6, 1988 [JP] Japan ................................. 63-224127
Feb. 28, 1989 [JP] Japan ................................... 1-48943

[51] Int. Cl.$^5$ ............................................ C07D 233/58
[52] U.S. Cl. ..................................................... 548/335
[58] Field of Search ......................................... 548/335

Primary Examiner—John M. Ford
Attorney, Agent, or Firm—Sherman and Shalloway

[57] ABSTRACT

Disclosed is a process for the preparation of a 1-benzylimidazole compound represented by the following general formula:

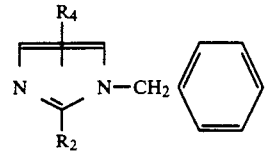

wherein $R_2$ represents a lower alkyl group or phenyl group, and $R_4$ represents a hydrogen atom or a methyl group, which comprises heating and to react a 1-unsubstituted imidazole compound represented by the following general formula:

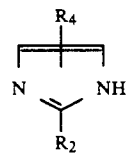

wherein $R_2$ and $R_4$ are as defined above, with benzyl alcohol in the presence of a carboxylic acid, a carboxylic anhydride, a benzyl ester thereof or a lower alkyl ester thereof, and neutralizing the reaction product with an alkali.

5 Claims, No Drawings

PROCESS FOR PREPARATION OF 1-BENZYLIMIDAZOLE COMPOUND

BACKGROUND OF THE INVENTION (1) Field of the Invention

The present invention relates to a process for preparing a 1-benzylimidazole compound by benzylation of a 1-unsubstituted imidazole, and also to a novel 1-benzylimidazole compound. The 1-benzylimidazole compound is valuable as a curing agent and a curing promoter for a polyepoxy resin.

(2) Description of the Related Art

A process for reacting a 1-unsubstituted imidazole compound with benzyl chloride, cooperating with an HC acceptor in an appropriate solvent having no active hydrogen atom is known [see, for example, Recl. Trev. Chim. Pays-Bas, Vol. 91, No. 12, 1383–1392 (1972)].

This benzylation process, however, involves the following problems. Namely, the 1-imidazole compound formed by the reaction between the 1-unsubstituted imidazole compound and benzyl chloride is likely to react further with unreacted benzyl chloride to form a 1,3-dibenzyl imidazolium chloride compound, and therefore, the unnecessary imidazolium chloride is formed as a by-product in a large quantity. Moreover, benzyl chloride is difficult to handle because of the lacrimatory property.

SUMMARY OF THE INVENTION

Under this background, we made research with a view to solving the above-mentioned problems, and as a result, it was found that a 1-benzylimidazole compound can be obtained at a high efficiency by heating to react a 1-unsubstituted imidazole compound with benzyl alcohol in the presence of a carboxylic acid, a carboxylic anhydride, a benzyl ester thereof or a lower alkyl ester thereof and neutralization of the reaction product with an alkali.

It was also found that a 1-benzylimidazole compound is similarly obtained by reactng a 1-unsubstituted imidazole compound with a benzyl ester of a carboxylic acid and neutralizing the reaction product with an alkali.

We have now completed the present invention based on these findings.

More specifically, in accordance with one aspect of the present invention, there is provided a process for the preparation of a 1-benzylimidazole compound represented by the following general formula:

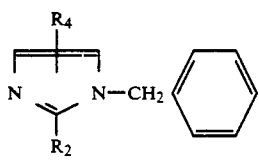

wherein $R_2$ represents a lower alkyl group or phenyl group, and $R_4$ represents a hydrogen atom or a methyl group, which comprises heating and to react a 1-unsubstituted imidazole compound represented by the following general formula:

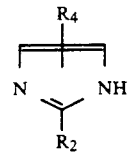

wherein $R_2$ and $R_4$ are as defined above, with benzyl alcohol in the presence of a carboxylic acid, a carboxylic anhydride, a benzyl ester thereof or a lower alkyl ester thereof, and neutralization of the reaction product with an alkali.

In accordance with another aspect of the present invention, there is provided a process for the preparation of a 1-benzylimidazole compound represented by the following general formula:

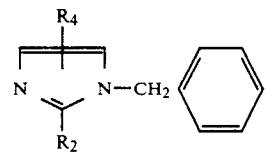

wherein $R_2$ represents a lower alkyl group or a phenyl group, and $R_4$ represents a hydrogen atom or a methyl group, which comprises heating to react a 1-unsubstituted imidazole compound represented by the following general formula

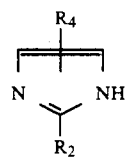

wherein $R_2$ and $R_4$ are as defined above, with a benzyl ester of a carboxylic acid and neutralization of the reaction product with an alkali.

DETAILED DESCRIPTION OF THE INVENTION

The preparation proces of the present invention is represented by the following reaction formulae:

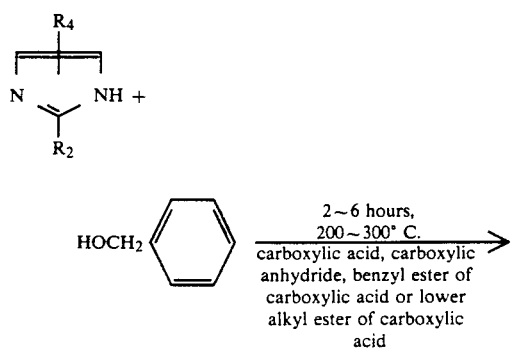

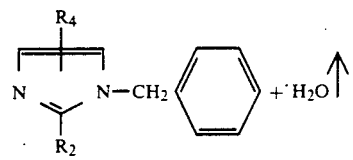

-continued

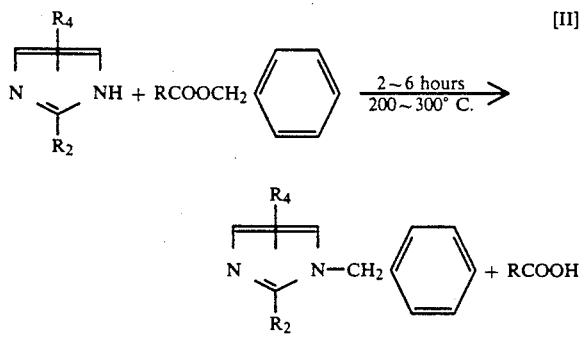

wherein $R_2$ represents a lower alkyl group or a phenyl group, $R_4$ represents a hydrogen atom or a methyl group, and R represents a carboxylic acid residue.

In the reaction of formula I, the carboxylic acid, carboxylic anhydride or benzyl or lower alkyl ester thereof is used in an amount of 0.01 to 1.0 mole, preferably 0.05 to 0.4 mole, per mole of the imidazole compound. Benzyl alcohol is used in an amount of 1.05 to 1.5 moles per mole of the imidazole compound. The reaction temperature is 200° to 300° C., preferably 230° to 260° C. In this case, the reaction is completed within 4 hours. The reaction can be carried out under atmospheric pressure or under such a reduced pressure that benzyl alcohol is not distilled. Water formed by the reaction is removed from the reaction system in the form of an azeotrope (boiling point=98° C.) by distillation. In order to remove a small amount of water that remains in the reaction mixture, the pressure is reduced to about 600 mmHg at the state where the reaction is sufficiently advanced, or scavenging is carried out by using an inert gas.

In the reaction of the present invention, a carboxylic acid, a carboxylic anhydride, a benzyl ester thereof and a lower alkyl ester thereof exert the catalytic action. This is a novel finding.

After an alkali hydroxide has been added to the reaction mixture in an amount sufficient to effect the neutralization, distillation is carried out under a reduced pressure, a crude intended 1-benzylimidazole compound can be obtained.

After an alkali hydroxide has been added to the crude compound in a molar quantity corresponding to the unreacted imidazole compound, distillation under a reduced pressure is carried out again, the intended compound substantially free of the unreacted imidazole compound can be obtained.

The carboxylic acid, the carboxylic anhydride and the benzyl ester thereof, are benzoic acid, phthalic acid, trimellitic acid, pyromellitic acid, isophthalic acid, terephthalic acid, succinic acid, maleic acid, adipic acid, and anhydrides and benzyl esters thereof (inclusive of semiesters of polycarboxylic acids).

The benzyl ester of the carboxylic acid is obtained by heating to react benzyl alcohol with a corresponding carboxylic anhydride or carboxylic acid. Accordingly, in carrying out the present invention, a carboxylic acid and benzyl alcohol can be used in combination instead of the carboxylic acid ester itself.

It is known that a lower alkyl ester of a carboxylic acid is easily ester-exchanged with benzyl alcohol to form a benzyl ester by heating (the low alkyl alcohol is distilled out of the reaction system because of its lower-boiling point).

Accordingly, a lower alkyl ester of a carboxylic acid, such as a methyl ester, an ethyl ester, a propyl ester, an isopropyl ester or a butyl ester can be used, in carrying out the present invention, respectively.

In the process represented by reaction formula [II], the benzyl ester of the carboxylic acid should be used in an amount equal to, or slightly larger than, the equivalent amount of the imidazole compound. The reaction temperature is generally 200° to 300° C. and preferably 230° to 260° C. In this case, the reaction is completed within 4 hours. After the carboxylic acid component of the reaction mixture has been neutralized with an alkali, an organic solvent (such as acetone) is added to the reaction mixture, and the mixture is filtered and the filtrate is subjected to distillation under a reduced pressure, whereby a crude intended 1benzylimidazole compound can be obtained. An alkali hydroxide is added to the crude intended compound in a molar quantity corresponding to the unreacted imidazole compound and distillation under a reduced pressure is carried out again, whereby an intended compound substantially free from the unreacted imidazole compound is obtained.

As the typical carboxylic acid used for the synthesis of the benzyl ester, there can be mentioned benzoic acid, phthalic acid, trimellitic acid, pyromellitic acid, isophthalic acid, terephthalic acid, maleic acid and adpic acid, and acid anhydrides thereof.

The benzyl ester (inclusive of a semiester) of the carboxylic acid can be obtained by heating benzyl alcohol with a corresponding carboxylic anhydride or carboxylic acid while distilling water formed by the reaction from the reaction system.

Typical imidazole compounds used in the present invention include 2-methylimidazole (hereinafter referred to as "2MZ"), 2-ethylimidazole (hereinafter referred to as "2RZ"), 2-isopropylimidazole (hereinafter referred to as "2IZ"), 2-phenylimidazole (hereinafter referred to as "2PZ"), 2-ethyl-4-methylimidazole (hereinafter referred to as "2E4MZ"), and 2-phenyl-4-methylimidazole (hereinafter referred to as "2P4MZ").

The properties of 1-benzylimidazoles prepared according to the process are described below. Incidentally, 1-benzyl-2-ethylimidazole, 1-benzyl-2-ethyl-4(5)-methylimidazole are novel compounds.

1-Benzyl-2-methylimidazole

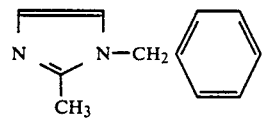

Neutral colorless crystal having a melting point of 48° to 52° C. (hexane) and being hardly soluble in water but easily soluble in alcohols, acetone and benzene, TLC (silica gel, methanol, $I_2$ coloration):

Rf=0.60 to 0.75

IR: $KBr_{cm}^{-1}$ 3400(19), 3030(23), 1675(30), 1610(35), 1590(37), 1530(29), 1500(24), 1475(26), 1455(24), 1430(22), 1360(28), 1290(25), 1205(47), 1160(32), 1135(30), 1080(38), 1035(33), 990(30), 932(47), 850(42), 730(21), 700(25), 680(29)

Each parenthesized value indicates the percent transmission.

1-Benzyl-2-ethylimidazole

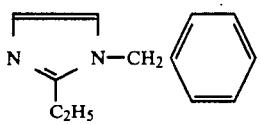

Weakly basic colorless liquid having a boiling point (bp24) of 186° to 191° C. can being insoluble in water but easily soluble in alcohols, acetone and chloroform.
TLC(silica gel, acetone, $I_2$ coloration):
Rf=0.32 to 0.45
IR $\nu$liquid film 3110(44), 3070(45), 3040(42),
$cm^{-1}$ 2980(32), 2940(37), 2880(45),
1603(48), 1520(43), 1495(23),
1451(24), 1428(26), 1370(45),
1353(41), 1330(47), 1273(34),
1180(53), 1150(43), 1120(48),
1070(42), 1040(42), 1025(45),
960(54), 910(53), 832(55),
720(20), 688(33)
Each parenthesized value indicates the percent transmission.
NMR(CDCl$_3$): $\delta$7.0–7.4, m, 5H; 6.98, S, 1H and 6.82 S, 1H; 5.04, S,2H; 2.63, q(J=7hz), 2H; 1.28, t(J=7Hz), 3H
Mass m/e: 186, 95, 91, 65

1-Benzyl02isopropylimidazole

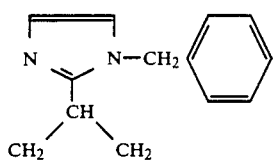

Basic light-yellow liquid having a boiling point (bp10) of 166° to 168° C. and being insoluble in water but easily soluble in alcohols, acetone and chloroform. TLC (silica gel, CHC$_3$/MeOH=9/1, B.T.B. coloration):
RF =0.60 to 0.80
IR: $\nu$liquid film $cm^{-1}$ 3100(52), 3060(53), 3030(48),
$cm^{-1}$ 2960(37), 2920(41), 2860(47),
1600(59), 1510(53), 1480(39),
1450(39), 1350(45), 1270(41),
1162(51), 1145(51), 1060(42),
1010(55), 710(41), 680(44)
Each parenthesized value indicates the percent transmission.
NMR(CDCl$_3$): $\delta$7.0–7.4, m, 5H(phenyl grup);
7.0, S, 1H and 6.8, S, 1H(4- and 5-positions);
5.1, S, 2H(methylene group); 2.9, septet, 1H; 1.2, d, 6H
Mass m/e: 201(M$^+$+1), 200(M$^+$), 185(M$^+$-CH$_3$), 157(M$^+$-isopropyl), 109(M$^+$-benzyl), 91(benzyl), 65

1-Benzyl-2-phenylimidazole

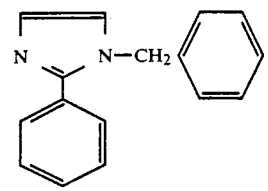

Neutral colorless crystal having a melting point of 51° to 53° C. (hexane) and being insoluble in water and hexane but easily soluble in alcohols, acetone and benzene.
TLC (silica gel, acetone, $I_2$ coloration):
RF=0.65 to 0.73
IR: $\nu$KBr 3100(38), 3055(35), 3025(36), 2920(40),
$cm^{-1}$ (1600(42), 1490(29), 1462(25), 1447(26),
1409(26), 1350(40), 1265(32), 1170(49),
1150(50), 1118(41), 1065(40), 1020*47),
1010(39), 990(51), 947(52), 903(46),
935(53), 760(28), 700(22), 682(16)
Each parenthesized value indicates the percent transmission.
NMR(CDCl$_3$): $\delta$b 7.54, (J=6Hz), 2H(imidazole ring); 7.4–6.9, m, 10H (phenyl); 5.21, S, 2H(methylene)
Mass m/e: 235(M$^+$+1), 234(M$^+$), 143, 91, 76, 65

1-Benzyl-2-ethyl04(5)-methylimidazole

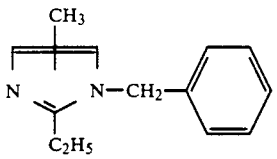

Resin colorless crystal having a molting point of to 72° C. (toluene) and being insoluble in water but easily soluble in alcohols, acetone and chloroform. TLC (silica gel, methanol, $I_2$ coloration):
Rf=0.60 to 0.70
IR: $\nu$liquid film 3360(31), 3030(34), 2970(20),
$cm^{-1}$ 2930(22), 2870(35), 1950(65),
1810(65), 1650(58), 1600(53),
1570(50), 1493(25), 1450(18),
1420(19), 1378(44), 1350(40),
1320(47), 1295(34), 1160(51),
1065(38), 1025(46), 1005(54),
980(60), 795(57), 725(22),
690(24)
NMR(CDCl$_3$): $\delta$7.35–7.28, m, 3H; 7.05 and 6.91, m, 2H (inclusive of isomers); 6.75 and
6.51, S, 1H (proton of imidazole ring, inclusive of isomers);
5.01 and 5.00, S, 2H (methylene, inclusive of isomers); 2.60, q, 2H methylene of ethyl); 2.20 and 2.07,
S, 3H (inclusive of isomers); 1.25, t, 3H (terminal methyl)
Mass m/e: 201(M$^+$+1), 200(M$^+$), 185(M$^+$-methyl), 171 (M$^+$-ethyl), 134, 109 (M$^+$-benzyl), 92, 91, 89, 76, 65, 51, 42, 40

1-Benzyl-2-phenyl-4(5)-methylimidazole

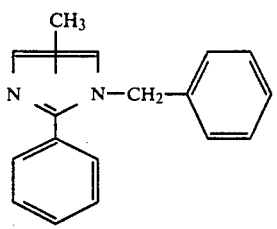

Neutral light-yellow crystal having a melting point of 62° to 64° C. (acetone) and being insoluble in water but easily soluble in alcohols, acetone and chloroform. TLC (silica gel, MeOH, $I_2$ coloration):
Rf=0.80 to 0.90
IR νliquid film 3660(50), 3380(28), 3070(23),
$cm^{-1}$ 3040(25), 2950(29), 2920(25),
1960(60), 1890(63); 1810(62),
1640(51), 1605(35), 1570(17),
1495(17), 1470( 9), 1450( 6),
1405( 6), 1355(20), 1300(29),
1250(51), 1160(30), 1073(31),
1021(26), 915(48), 840(59),
800(38), 765( 9), 725( 9),
705(10), 690( 4)
NMR($CDCl_3$): δ7.56–7.46 and 7.40–7.23 and 7.10–7.00,
m, 10H; 6.64, S, 1H
(imidazole ring); 5.10, B, 2H
(methylene); 2.24, S, 3H (methyl)
Mass m/e: 249($M^+ +1$), 248($M^+$), 158, 157, 101, 91, 59, 58, 56, 55, 46, 45, 43, 41, 39, 31

The present invention will now be described in detail with reference to the following examples that by no means limit the scope of the invention.

EXAMPLES 1 THROUGH 25

A predetermined amount of a carboxylic acid, a carboxylic anhydride or a lower alkyl ester of a carboxylic acid is mixed with 0.1 mole of a 1-unsubstituted imidazole and 0.11 mole of benzl alcohol, and heating reaction was carried out under predetermined conditions. Then, an alkali was added to the reaction mixture to effect neutralization and salting-out. The formed oil layer was separated and collected, and the extract was subjected to distillation under a reduced pressure singly or in the presence of NaOH to obtain a crude intended 1-benzylimidazole compound. The experimental conditions and obtained results are shown in Table 1.

Incidentally, runs where benzyl alcohol was first esterified with a carboxylic acid, a 1-unsubstituted imidazole compound was added to the reaction system and heating reaction was then carried out are indicated by "esterification precedent" in column "Remarks".

When each of the obtained crude intended compounds was examined by TLC (silica gel/acetone), it was found that each crude intended compound contained only a very small amount of the unreacted imidazole.

TABLE 1

| Example No. | Imidazole | Carboxylic Acid | (mole) | Reaction Temperature (°C.) |
| --- | --- | --- | --- | --- |
| 1 | 2EZ | trimellitic acid | (0.005) | 250 |
| 2 | 2EZ | trimellitic acid | (0.005) | 250 |
| 3 | 2EZ | trimellitic acid | (0.005) | 250 |
| 4 | 2EZ | trimellitic acid | (0.01) | 250 |
| 5 | 2EZ | trimellitic acid | (0.02) | 250 |
| 6 | 2EZ | trimellitic acid | (0.03) | 250 |
| 7 | 2EZ | trimellitic acid | (0.04) | 250 |
| 8 | 2EZ | trimellitic anhydride | (0.01) | 250 |
| 9 | 2EZ | phthalic acid | (0.03) | 250 |
| 10 | 2EZ | phthalic anhydride | (0.01) | 250 |
| 11 | 2EZ | isophthalic acid | (0.01) | 250 |
| 12 | 2EZ | isophthalic acid | (0.03) | 250 |
| 13 | 2EZ | terephthalic acid | (0.01) | 230≈260 |
| 14 | 2EZ | pyromellitic acid | (0.03) | 250 |
| 15 | 2EZ | benzoic acid | (0.03) | 250 |
| 16 | 2EZ | succinic acid | (0.01) | 250 |
| 17 | 2EZ | malic acid | (0.03) | 250 |
| 18 | 2EZ | adipic acid | (0.03) | 250 |
| 19 | 2EZ | monomethyl phthalate | (0.01) | 250 |
| 20 | 2MZ | trimellitic acid | (0.02) | 250 |
| 21 | 2MZ | terephthalic acid | (0.03) | 250 |
| 22 | 2IZ | phthalic anhydride | (0.01) | 250 |
| 23 | 2E4MZ | phthalic anhydride | (0.01) | 250 |
| 24 | 2PZ | phthalic anhydride | (0.01) | 250 |
| 25 | 2P4MZ | trimellitic acid | (0.01) | 250 |

| Example No. | Reaction Time(hours) | Post Treatment Conditions | Yield (mole %) | Remarks |
| --- | --- | --- | --- | --- |
| 1 | 4 | NaOH 1.6 g, water 20 ml | 76.3 | |
| 2 | 4 | not neutralized | 72.0 | |
| 3 | 4 | in the presence of NaOH 1.0 g | 84.0 | esterification precedent |
| 4 | 4 | in the presence of NaOH 1.2 g | 68.0 | |
| 5 | 4 | NaOH 1.6 g, water 20 ml | 76.3 | |
| 6 | 3.5 | $NH_4OH$ | 74.7 | |
| 7 | 4 | NaOH 1.6 g, water 30 ml | 69.3 | |
| 8 | 4 | in the presence of NaOH 1.6 g | 65.0 | |
| 9 | 3 | $NH_4OH$ | 87.6 | |

TABLE 1-continued

| | | | | |
|---|---|---|---|---|
| 10 | 4 | in the presence of NaOH 1.0 g | 88.0 | |
| 11 | 10 | in the presence of NaOH 1.2 g | 76.9 | esterification precedent |
| 12 | 6 | NH₄OH | 76.0 | |
| 13 | 8 | in the presence of NaOH 1.0 g | 74.7 | |
| 14 | 3 | NH₄OH | 74.0 | |
| 15 | 4 | NH₄OH | 87.6 | |
| 16 | 4 | in the presence of NaOH 1.0 g | 74.0 | |
| 17 | 3.5 | NH₄OH | 71.0 | |
| 18 | 3 | NH₄OH | 55.0 | |
| 19 | 4 | in the presence of NaOH 1.2 g | 76.9 | |
| 20 | 3.5 | NH₄OH | 59.3 | |
| 21 | 5 | NH₄OH | 83.7 | |
| 22 | 4 | in the presence of NaOH 0.8 g | 84.0 | |
| 23 | 4.5 | in the presence of NaOH 1.0 g | 67.5 | esterification precedent |
| 24 | 5 | in the presence of NaOH 1.0 g | 81.0 | |
| 25 | 5 | in the presence of NaOH 1.0 g | 74.0 | |

EXAMPLES 26 THROUGH 34

A benzyl ester of a carboxylic acid was added to 0.1 mole of a 1-unsubstituted imidazole compound in an amount equivalent to the amount of the imidazole compound (3.3 equivalents), and heating reaction was carried out under predetermined conditions and the reaction mixtue was subjected to neutralization and salting-out wih an alkali. The formed oil layer was separated and collected. Then, neutralization was carried out according to need, and the mixture was dried to the solid under a reduced pressure, extracted with methanol and subjected to distillation under a reduced pressure to obtain a crude intended 1-benzylimidazole compound. The experimental conditions and obtained results are shown in Table 2. When the crude intended compound was examined by the thin layer chromatography in the same manner as in the preceding examples, it was found that only a very small amount of the unreacted imidazole was contained as an impurity.

TABLE 2

| Example No. | Imidazole | Benzyl Ester of Carboxylic Acid | Reaction Temperature (°C.) | Reaction Time (hours) | Yield (mole %) | Remarks |
|---|---|---|---|---|---|---|
| 26 | 2EZ | monobenzyl phthalate | 250 | 4 | 63 | drying to solid and extraction with methanol after neutralization |
| 27 | 2EZ | dibenzyl phthalate | 250 | 2 | 50 | drying to solid and extraction with methanol after neutralization |
| 28 | 2EZ | dibenzyl maleate | 250 | 4 | 72 | neutralization and salting-out |
| 29 | 2EZ | dibenzyl adipate | 250 | 4 | 78 | neutralization and salting-out |
| 30 | 2MZ | benzyl benzoate | 250 | 4 | 58 | neutralization and salting-out |
| 31 | 2MZ | dibenzyl terephthalate | 250 | 6 | 50 | neutralization and salting-out |
| 32 | 2MZ | dibenzyl isophthalate | 250 | 4 | 73 | neutralization and salting-out |
| 33 | 2IZ | tribenzyl trimellitate | 250 | 4 | 78 | drying to solid and extraction with methanol after neutralization |
| 34 | 2E4MZ | dibenzyl succinate | 250 | 4 | 72 | neutralization and salting-out |

REFERENTIAL EXAMPLE 1

Curing performances of 1-benzylimidazole compounds to liquid polyepoxy resins were examined.

A predetermined amount of a 1-benzylimidazole compound obtained according to the present invention was added as a curing agent to 100 parts by weight of a polyepoxy resin (Epikote #828 supplied by Yuka-Shell Epoxy), and the composition was cast into a space of 3 mm between two glass sheets. The case composition was maintained at 100° C., and the temperature was elevated to 150° C. and heating was conducted for 4 hours to effect curing.

The storage stability and gel time of each composition and the properties of the cured product were examined. The obtained results are shown in Table 3.

TABLE 3

| | $\begin{array}{c} R_4 \\ \| \\ N \underset{\|}{\overset{}{\diagdown}} N-CH_2-C_6H_5 \\ R_2 \end{array}$ | $-CH\begin{array}{c}CH_3\\ \diagdown \\ \diagup \\ CH_3\end{array}$ | $-C_2H_5$ | $-C_2H_5$ | $-C_6H_5$ |
|---|---|---|---|---|---|
| | $R_2$ | H | H | $-CH_3$ | $-CH_3$ |
| | $R_4$ | | | | |
| Amount (parts by weight) | | 10 | 3 | 5 | 10 |
| Storage Stability*1 | | 1.09 | 7.44 | 1.65 | 1.27 |
| Gel Time (hot plate method, 150° C.) | | 8'26" | 2'18" | 3'58" | 2'36" |
| Glass Transition Temperature (TMA method, °C.) | | 147 | 131 | 119 | 131 |
| Linear Expansion Coefficient (deg$^{-1}$, 25° C.) | | $61 \times 10^{-6}$ | $72 \times 10^{-6}$ | $72 \times 10^{-6}$ | $69 \times 10^{-6}$ |
| Volume Resistivity ($\Omega \cdot$ cm, 25° C.) | | $8 \times 10^{15}$ | $2 \times 10^{15}$ | $5 \times 10^{15}$ | $2 \times 10^{15}$ |
| Dielectric Constant (60Hz, 25° C.) | | 2.93 | 3.04 | 3.71 | 3.23 |
| Dielectric Loss (60Hz, 25° C., %) | | 0.24 | 0.37 | 0.54 | 0.54 |
| Flexural Strength (Kgf/cm$^2$, 25° C.) | | 7.1 | 6.6 | 7.9 | 11.1 |
| Flexural Modulus (Kgf/cm$^2$, 25° C.) | | 361 | 290 | 332 | 297 |
| Boiling Water Absorption (8 hours' boiling, % by weight) | | 0.99 | 0.86 | 0.72 | 0.80 |

Note
*1 ratio of viscosity of composition after standing for 24 hours at 25° C. to initial value of viscosity

REFERENTIAL EXAMPLE 2

Curing-promoting performances of 1-benzylimidazole compounds to acid anhydrides were examined.

A composition comprising 100 parts by weight of a polyepoxy resin (#Epikote #828 supplied by Yuka-Shell Epoxy), 87.4 parts by weight methyl-Δ$^4$-tetrahydrophthalic anhydride (Epichlon B570 supplied by Dai-Nippon Ink Kagaku Kogyo) and 0.5 part by weight of an imidazole compound was cast in a space of 3 mm between two glass sheets. The cast composition was maintained at 100° C. for 2 hours, and the temperature was elevated to 150° C. and the composition was heated for 4 hours to effect curing.

The storage stability and gel time of each composition and the properties of the cured product were examined. The obtained results are shown in Table 4.

The presence of a gelatinous substance (the salt of the acid anhydride with the imidazole) was not found in any composition.

TABLE 4

| | $\begin{array}{c} R_4 \\ \| \\ N \underset{\|}{\overset{}{\diagdown}} N-CH_2-C_6H_5 \\ R_2 \end{array}$ | $-CH\begin{array}{c}CH_3\\ \diagdown \\ \diagup \\ CH_3\end{array}$ | $-C_2H_5$ | $-C_2H_5$ | $-C_6H_5$ |
|---|---|---|---|---|---|
| | $R_2$ | H | H | $-CH_3$ | $-CH_3$ |
| | $R_4$ | | | | |
| Storage Stability*1 | | 2.71 | 4.33 | 2.61 | 2.60 |
| Gel Time*2 | | 19'30" | 17'24" | 16'39" | 18'18" |
| Glass Transition Temperature (TMA method, °C.) | | 126 | 129 | 120 | 122 |
| Linear Expansion Coefficient (deg$^{-1}$, 25° C.) | | $65 \times 10^{-6}$ | $59 \times 10^{-6}$ | $66 \times 10^{-6}$ | $58 \times 10^{-6}$ |
| Volume Resistivity ($\Omega \cdot$ cm, 25° C.) | | $2 \times 10^{16}$ | $1 \times 10^{16}$ | $4 \times 10^{15}$ | $7 \times 10^{15}$ |
| Dielectric Constant (60Hz, 25° C.) | | 2.91 | 2.82 | 3.57 | 3.13 |
| Dielectric Loss (60Hz, 25° C., %) | | 0.53 | 0.58 | 0.84 | 0.74 |
| Flexural Strength (Kgf/cm$^2$, 25° C.) | | 14.5 | 13.6 | 13.2 | 13.8 |
| Flexural Modulus (Kgf/cm$^2$, 25° C.) | | 349 | 318 | 327 | 371 |
| Boiling Water Absorption (4 hours' boiling, % by weight) | | 0.64 | 0.73 | 0.53 | 0.57 |

Note
*1 ratio of viscosity after standing at 40° C. for 24 hours to initial value of viscosity
*2 time required for stopping of rotational viscometer when composition was maintained at 120° C.

We claim:

1. A process for the preparation of a 1-benzylimidazole compound represented by the following formula:

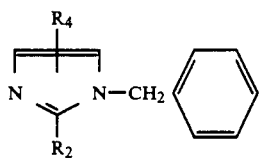

wherein $R_2$ represents a lower alkyl group or phenyl group, and $R_4$ represents a hydrogen atom or a methyl group,
which comprises heating a 1-unsubstituted imidazole compound represented by the following formula:

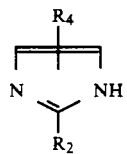

wherein $R_2$ and $R_4$ are as defined above, with benzyl alcohol in the presence of a carboxylic acid, a carboxylic anhydride, a benzyl ester thereof or a lower alkyl ester thereof, and neutralizing the reaction product with an alkali.

2. A process for the preparation of a 1-benzylimidazole compound represented by the following formula:

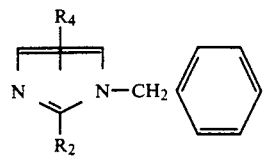

wherein $R_2$ represents a lower alkyl group or a phenyl group, and $R_4$ represents a hydrogen atom or a methyl group,
which comprises heating a 1-unsubstituted imidazole compound represented by the following formula:

wherein $R_2$ and $R_4$ are as defined above, with a benzyl ester of a carboxylic acid and neutralizing the reaction product with an alkali.

3. 1-Benzyl-2-ethylimidazole.

4. A compound selected from the group consisting of 1-benzyl-2-ethyl-4-methylimidazole and 1-benzyl-2-ethyl-5-methylimidazole.

5. A compound selected from the group consisting of 1-benzyl-2-phenyl-4-methylimidazole and 1-benzyl-2-ethyl-5-methylimidazole.

* * * * *